United States Patent [19]

Bonchek

[11] 4,329,985
[45] May 18, 1982

[54] VEIN DISTENTION SYSTEM

[75] Inventor: Lawrence I. Bonchek, Milwaukee, Wis.

[73] Assignee: Shiley, Inc., Irvine, Calif.

[21] Appl. No.: 113,247

[22] Filed: Jan. 18, 1980

[51] Int. Cl.³ .............................................. A61M 5/00
[52] U.S. Cl. ............................................... 128/214 R
[58] Field of Search .......... 128/207.28, 214 R, 214 E, 128/341, 128, 218 R, 234, 673, 748, 214 F

[56] References Cited

U.S. PATENT DOCUMENTS

| | | | |
|---|---|---|---|
| 1,316,394 | 9/1916 | Sellar | 128/214 X |
| 1,427,515 | 8/1922 | Capell | 128/207.28 |
| 1,541,615 | 6/1925 | Bessesen | 128/214 X |
| 1,869,443 | 8/1932 | Stocklin | 128/214 X |
| 2,646,042 | 6/1953 | Hsi Hu | 128/214 |
| 3,407,817 | 10/1968 | Galleher | 128/351 |
| 3,543,751 | 12/1970 | Sheffer | 128/208 |
| 3,543,759 | 12/1970 | McWhorter | 128/349 |
| 3,599,620 | 8/1971 | Ballin | 128/349 B |
| 3,625,199 | 12/1971 | Summers | 128/2 R |
| 3,642,005 | 2/1972 | McGinnis | 128/351 |
| 3,794,043 | 2/1974 | McGlinnis | 128/349 BV |
| 3,916,874 | 11/1975 | Perrin | 128/1 R |
| 3,958,557 | 5/1976 | Sharp et al. | 128/1 R |
| 4,000,741 | 1/1977 | Binard et al. | 128/218 |
| 4,135,494 | 3/1977 | Stoner et al. | 128/1 R |

FOREIGN PATENT DOCUMENTS 2916097 4/1979 Fed. Rep. of Germany ............ 128/

Primary Examiner—Gene Mancene
Assistant Examiner—Wenceslao J. Contreras
Attorney, Agent, or Firm—Knobbe, Martens

[57] ABSTRACT

Apparatus for the distention and irrigation of a saphenous vein which is being tested prior to use as a coronary or peripheral bypass graft includes a specially-configured cannula for insertion into the vein, and a pressure-limiting device having a resilient membrane reservoir which limits the hydrostatic pressure delivered to the vein to a predetermined level. The device is connected between the cannula inserted into the vein and a syringe filled with irrigation fluid. As fluid is delivered under pressure from the syringe, the membrane reservoir fills with fluid and inflates within a specified range of pressures so that if excessive force is applied to the syringe, the membrane inflates, and the pressure transmitted to the vein cannot exceed a predetermined maximum pressure. A stopcock connected between the syringe and the membrane allows the membrane to be pressurized with the contents of the syringe. With the membrane filled and pressurized, the stopcock is closed, allowing the membrane to act as a reservoir which irrigates the vein at a constant, controlled pressure without further use of the syringe. The cannula has a tapered and bevelled tip which allows easy insertion into the vein, and a sloping shoulder just proximal to the tip which provides a convenient site for firmly securing the vein of the cannula with a ligature.

18 Claims, 6 Drawing Figures

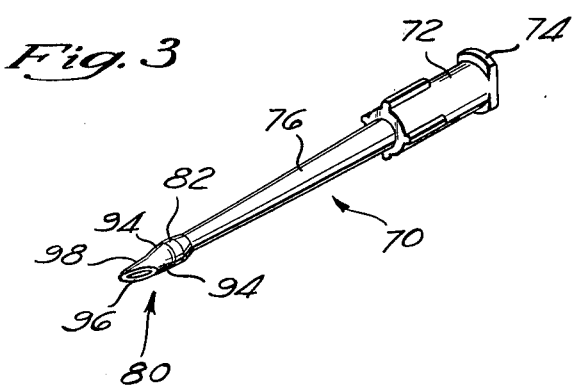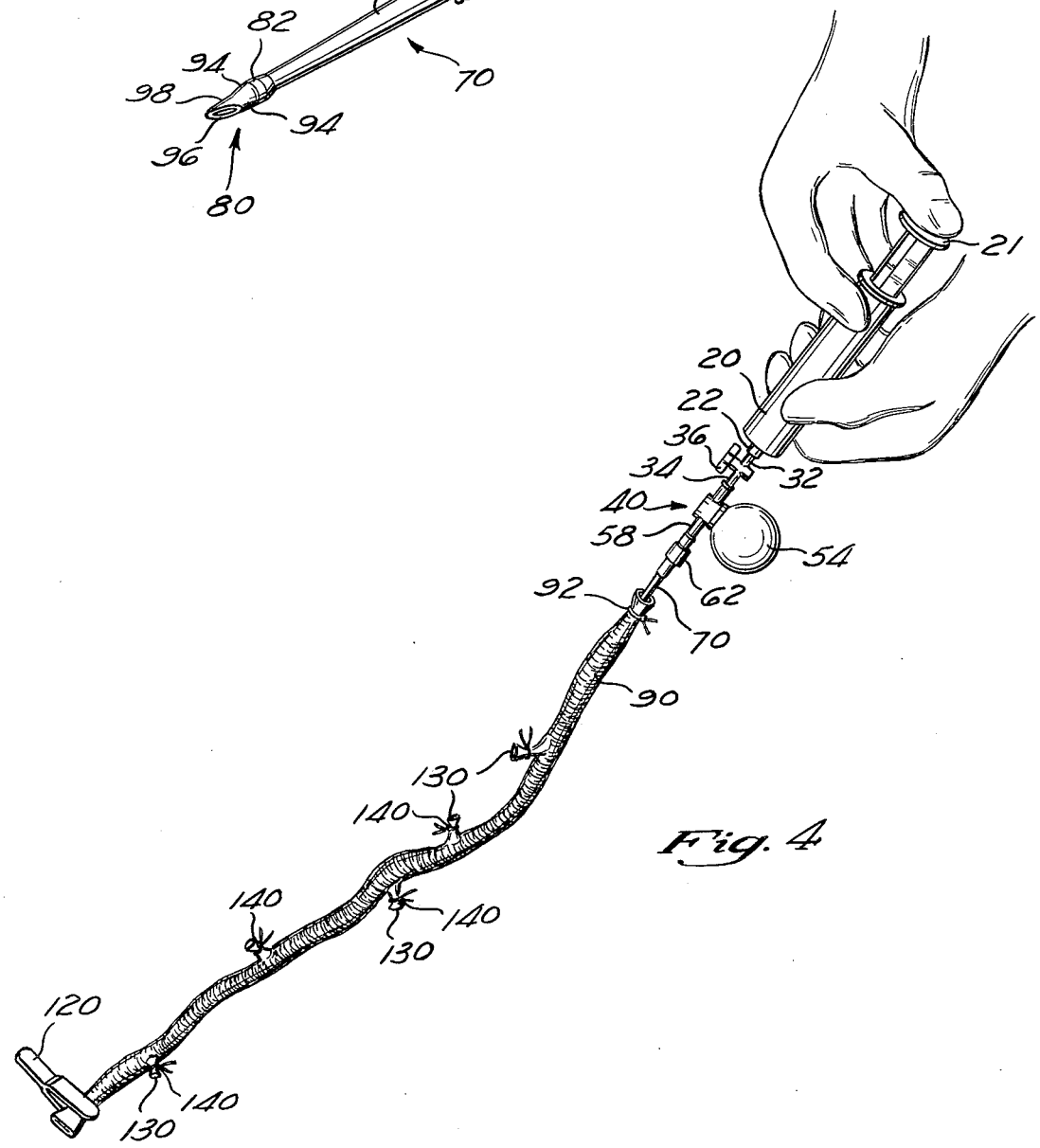

VEIN DISTENTION SYSTEM

BACKGROUND OF THE INVENTION

This invention relates to apparatus for the distention and irrigation of veins in preparation for transplantation within the human body. In particular, it relates to a device for the distention of the saphenous vein with a controlled pressure, thereby avoiding tissue damage within the vein, prior to implantation as a coronary or peripheral bypass graft.

The use of autogeneous vein grafts in arterial bypass surgery has become a well-known procedure in the treatment of degenerative disorders in the coronary circulation system, and the saphenous vein in the leg is the preferred candidate for these grafts.

In the preparation of a vein segment for the grafting procedure, it is necessary to distend the vein segment after removal from the patient's leg in order to overcome spasm and to identify leaky side branches. Typically, this is done by tying off the upstream end of the vein segment and injecting irrigation fluid (typically a saline solution) into the open downstream end manually by means of a syringe. The typical procedure is described in some detail in U.S. Pat. No. 3,958,557 to Sharp, et al.

It has become known in recent years that distention of the veins at pressures in excess of 500 millimeters of mercury (mm Hg) can damage the vascular endothelium, with a resultant premature loss of vein patency subsequent to the bypass implantation. Thus, it has been established that excessive pressurization during distention can ultimately result in premature failure of the grafted vein segment due to thrombosis, subendothelial hyperplasia, or accelerated atherosclerosis.

Consequently, extreme care must be taken in the distention procedure to avoid excessive pressurization. Until recently, the degree of success achieved in this regard depended solely upon the judgment and skill of the operator performing the procedure. However, it was found that even the most skillful practitioner could not readily detect the relatively high pressures (600 to 700 mm Hg) generated by the syringe, because a vein in spasm has a small diameter and a low wall tension (Laplace's Law).

Thus, it has become apparent that some means is necessary for reliably limiting the distention pressure to a value below 500 mm Hg. In addition, recent experiments have demonstrated that distention pressures in the range of 100 to 400 mm Hg are necessary both to overcome spasm in most veins, and to reveal reliably all unsecured side branches in the vein segments involved. In some cases, static pressures of 400 mm Hg have been found to facilitate complete vein dilation, and transient pressures as high as 500 mm Hg have been used to dilate particularly spastic vein segments. The experiments demonstrated that static pressures in the range of 100 to 400 mm Hg were well tolerated, producing little, if any, noticeable vein damage.

The results of these experiments indicated the need to provide static distention pressures in the range of 100 to 400 mm Hg, with the further need to allow transient pressures up to, but not substantially in excess of, 500 mm Hg. As previously noted, such static pressures allow substantially complete identification of all unsecured side branches. These side branches are preferably secured during the irrigation procedure, to ensure that none are overlooked.

In the prior art, continuous pressure must, typically, be supplied by the syringe. Thus, the person performing the distention procedure is not able, simultaneously, to secure the side branches, and an additional practitioner is necessary to perform this latter operation. Accordingly, it is desirable to have some means for automatically delivering the irrigation fluid, at the desired pressure, without the continued need for the syringe, thereby allowing a single practitioner first to initiate the irrigation, and then to secure the side branches while the irrigation continues under automatically controlled pressure.

The prior art has taught the desirability of injecting the irrigation fluid into the vein through a cannula inserted into the open end of the vein and secured thereto by a temporary ligature. One such cannula is disclosed in the aforementioned patent to Sharp et al. It has become the usual practice to cannulate the open upstream end of the saphenous vein before the downstream end is removed from the patient's leg. The open end of the vein remains cannulated throughout the irrigation and distention operation, until just before implantation of the vein segment as a coronary bypass. In this manner, the cannula provides easy identification of the respective ends of the vein, an important consideration since the valves in the vein allow blood flow in only one direction.

The typical prior art cannula has a blunt, circular leading edge on its tip, which is normally tapered to have an outside diameter at the leading edge which is approximately equal to the undistended inside diameter of the vein. The cannula may also include a peripheral flange to facilitate a temporary fluid-tight ligation of the vein on the cannula. It has been found that the blunt, circular leading edge of such a cannula is very difficult to insert into the vein, making this maneuver tedious and unnecessarily prolonged.

SUMMARY OF THE INVENTION

Broadly, the present invention is a pressure-limiting vein distention and irrigation system for attachment to a standard irrigation syringe. The principal component in the system is a pressure-limiting device having a fluid inlet portion for receiving irrigation fluid from the syringe, a fluid outlet portion, and a resilient, balloon-like bulbous reservoir in fluid communication with both the inlet and outlet portions.

Detachably connected between the inlet portion of the pressure-limiting device and the outlet nozzle of the syringe is a short tubular section having a stopcock, and detachably connected to the outlet portion of the pressure-limiting device is a specially-configured cannula, having a tapered and bevelled distal end or tip which provides both easy insertion into the open proximal end of the saphenous vein, and secure retention in the vein during the distention procedure. This cannula is described in more detail and claimed in a divisional application entitled "Cannula for Vein Distention System", Ser. No. 147,847, filed May 8, 1980, assigned to Shiley, Inc.

The material, configuration, and dimensions of the resilient reservoir of the pressure-limiting device are selected so that the reservoir inflates within a specified range of pressures when it is filled with the contents of the syringe. This expansion of the reservoir assures that the hydrostatic pressure applied to the vein through the cannula cannot exceed the peak pressure attained in this pressure range. Thus, if excessive force is applied to the syringe, the reservoir begins to inflate, and the pressure transmitted to the vein cannot exceed the predetermined limit set by the expansion of the reservoir. In keeping with the clinical findings noted earlier, the reservoir is selected to have a predetermined inflation pressure of somewhere in the range of 100 to 400 mm Hg, depending upon the needs or preferences of the operator.

The use of the stopcock allows a controlled, substantially constant-pressure flow of fluid to be delivered to the vein without the need for the operator constantly to apply pressure to the syringe. To accomplish this, the reservoir is first pressurized by filling it with the entire contents of the syringe (after the vein has been "primed" with fluid). The stopcock is then closed, and the reservoir delivers fluid to the vein at the desired pressure automatically, without further need of the syringe. The operator now has both hands free to control the unsecured side branches of the vein, and manually to compress specific vein segments to treat localized areas of persistent spasm.

Although the pressure-limiting device of the present invention can be used with standard vein irrigation cannulae, it is most advantageously used as a system with a specially-configured cannula, designed to achieve easy insertion into the open, proximal end of the saphenous vein without unnecessary injury thereto, while at the same time providing secure retention within the venous lumen. These advantages are achieved with a design in which the distal end or tip of the cannula is tapered down slightly from an outside diameter approximately equal to the undistended inside diameter of the vein, and which is obliquely bevelled to present a narrow, arcuate (rather than circular) leading edge. The cannula is further provided with a gently-sloping shoulder just proximally of the tip. This shoulder provides a convenient site for a temporary fluid-tight ligation of the vein upon the cannula.

Thus, the present invention provides a system for saphenous vein distention and irrigation which substantially eliminates the two major causes of vein trauma which plagued the prior art: over-pressurization, and non-subtle cannulation. Moreover, the present invention provides optimal distention pressures for spasm elimination and leak detection, while allowing the operator to have both hands free to secure leaky side branches and to manipulate manually overly spastic portions of the subject vein segment.

BRIEF DESCRIPTION OF THE DRAWINGS

FIG. 3 is a perspective view of the cannula of the present invention;

FIG. 4 is a perspective view of a saphenous vein being irrigated and distended by use of the present invention;

DETAILED DESCRIPTION OF THE INVENTION STRUCTURE OF THE OVERALL SYSTEM

Figure 1:
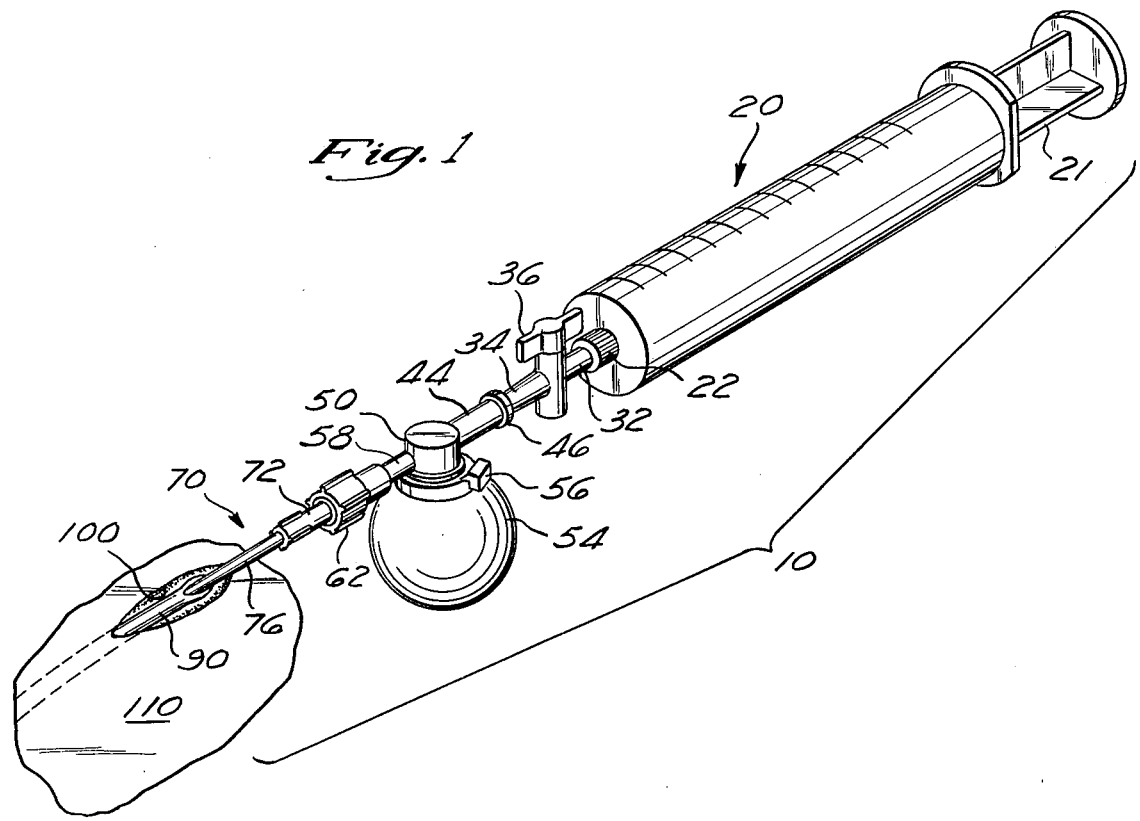
FIG. 1 is a perspective view of a vein distention system of the present invention, showing the invention in position upon cannulation of the saphenous vein of a patient.

Referring just to FIG. 1, a vein distention and irrigation system 10 in accordance with the invention is shown. The major components of the system are a syringe 20, a valving member 30, a pressure-limiting device 40, and a cannula 70.

The syringe 20 is a typical disposable surgical syringe, preferably having a fluid capacity of about 60 cc. The syringe 20 has a plunger 21, and should be of the type having a Luer-lock nozzle 22, to provide a secure, fluid tight connection to the valving member 30.

The valving member 30 comprises basically a hollow tubular member having an inlet 32 adapted for connection to the Luerlock nozzle 22 of the syringe 20, and an outlet 34. Between the inlet 32 and the outlet 34 is a stopcock 36 for opening and closing the passage (not shown) between the inlet 32 and the outlet 34.

Figure 2:
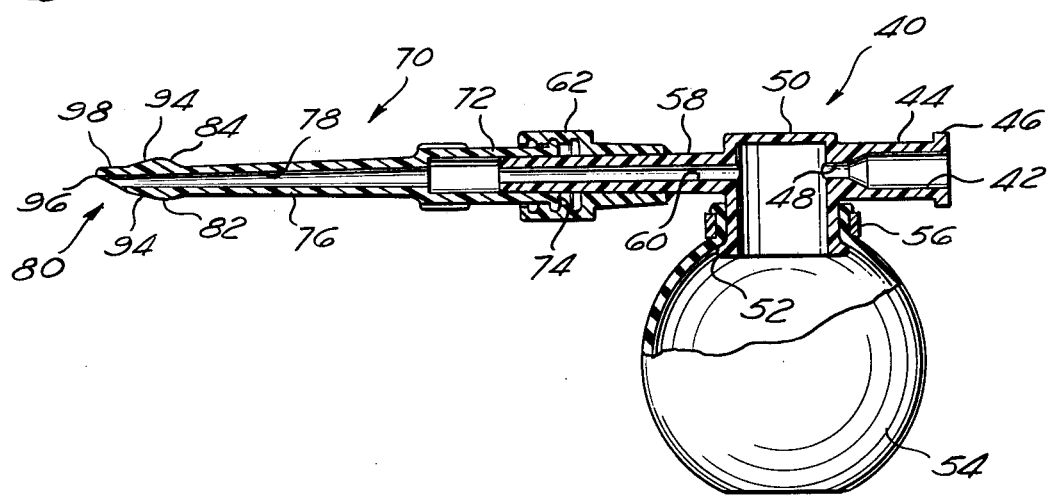
FIG. 2 is a cross-sectional view of the cannula and the pressure-limiting device used in the present invention.

The outlet 34 of the valving member 30 is slightly tapered to facilitate insertion into the bore 42 of an inlet section 44 of the pressure-limiting device 40. As best shown in FIG. 2, the inlet section 44 is advantageously provided with a peripheral flange 46 so that the pressure-limiting device 40 can be attached directly to the syringe 20 by means of the Luerlock 22, if it is desired to do without the valving member 30.

Referring now to FIG. 2, the bore 42 of the inlet section communicates, via a reduced diameter passage 48, with a substantially cylindrical vertical chamber 50 which is open at one end (the bottom, as shown in FIG. 2). Surrounding the open (bottom) end of the chamber 50 is a peripheral lip or flange 52.

Secured over the open end of the chamber 50 around the flange 52 is a balloon-like, expandable reservoir 54, made of a resilient material, preferably latex. The reservoir 54 may be attached to the chamber 50 by means such as a nylon tie 56 as shown, or it may be glued or bonded directly to the chamber 50. The functional characteristics of the reservoir 54 will be discussed in detail below.

Extending from the side of the chamber 50 opposite the inlet section 44 is a tubular outlet section 58 having a central passage 60 communicating with the interior of the chamber 50. Attached to the distal (i.e., away from the syringe 20) end of the outlet section 58 is a Luerlock fitting 62.

While the pressure-limiting device may be made of any number of materials, the inlet section 44, chamber 50, and outlet section 58 are preferably made as an integral unit of a rigid plastic material. An excellent example is a polycarbonate resin plastic such as that marketed under the trade name Lexan by General Electric Corporation. This material is rigid, easily formed, inexpensive, and naturally transparent, making it most suitable for a disposable unit.

The proximal (toward the syringe) portion of the cannula 70 comprises a tubular female fitting 72 adapted to receive the distal end of the outlet section 58 of the pressure-limiting device 40. The proximal end of the fitting 72 is provided with a peripheral flange 74 adapted to be lockably engaged in the Luerlock fitting 62. (See FIG. 2).

Most of the length of the cannula 70 is comprised of a tubular body or stylet 76 having a slight taper in outside diameter from its proximal to its distal end. The stylet or body 76 has a central fluid passageway or bore 78 (FIG. 2).

Figure 6:
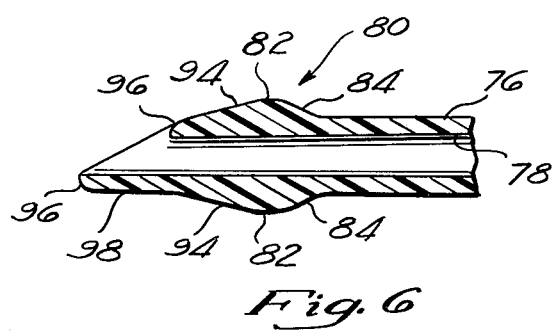
FIG. 6 is a longitudinal cross-sectional view of the tip of the cannula used in the present invention.

The major novelty of the cannula resides in its specially configured tip 80, shown in FIGS. 2, 3, and 6. The proximal end of the tip 80 slopes radially outwardly at an angle of between about 20° and 30° (25° optimally) to form a rounded peripheral ridge 82 around the exterior of the tip 80. The outside diameter of the ridge 82 is preferably approximately equal to, or slightly larger than, the nominal undistended inside diameter of a typical vein graft, so that the cannula, once inserted into the venous lumen, is retained therein. The sloping proximal side of the ridge thus forms a shoulder 84 (FIGS. 2 and 6) which provides a convenient site for tying the open upstream end of a saphenous vein segment (designated by the numeral 90 in FIG. 4) to the cannula 70 by means of a temporary ligature 92, to provide a fluid-tight seal.

Distally from the ridge 82, the tip 80 has a slightly tapered portion 94, which tapers radially inwardly at an angle of between about 7° and 15° (11° optimally). This tapered section 94 is terminated on one side of the tip 80 by the proximal side of an oblique or bevelled leading edge 96. The diametrically opposite side of the tapered section 94 is terminated by an untapered, axially-extending section 98 which extends to the distal side of the leading edge 96. Thus, as best shown in FIGS. 3 and 6, the cross-sectional shape of the leading edge rather than being circular, is a relatively narrow, arcuate or rounded "point", permitting easy insertion of the cannula into the open upstream end of the vein 90 (FIGS. 1 and 4) with minimal damage to the vein wall tissue.

The cannula 70 is preferably an integral unit of a plastic, such as poly(ethylene terephthalate) copolyester sold by Eastman Kodak. It should be noted that the tip 80 has no sharp corners or edges, either between the various sections described above or along the leading edge 96, all such corners and edges being rounded. Such a design thus significantly facilitates insertion of the cannula. Moreover, since the ligature site is the sloping shoulder 84, rather than a ridge or flange as in the prior art, the vein can be securely tied to the cannula without risk of significant trauma, and the proximally-directed forces on the cannula in response to the injection of the fluid into the vein likewise presents little or no risk of vein wall damage.

DESCRIPTION OF FUNCTION AND METHOD OF USE

As in the prior art, the harvesting of a segment of the great saphenous vein using the present invention begins with making an incision 100 in the leg 110 of a patient to expose the lower or upstream end of the great saphenous vein 90. (See FIG. 1.) The incision severs the upstream end of the vein, leaving it open for the insertion of the cannula 70. The cannula is inserted at this early stage, prior to removal of the vein from the patient's leg, so that the upstream end of the vein is clearly designated throughout the procedure, thereby allowing the vein to be oriented properly when it is grafted as an arterial bypass, since the valves in the vein allow fluid flow in only one direction. A segment of the vein 90, of the required length, may then be removed by extending the incision 100 upwardly along the patient's thigh.

The syringe 20 is filled with approximately 50 to 60 cc of irrigation fluid. Typically, this fluid has been a saline solution, but recently it has become the preferred practice to use the patient's own blood, or a mixture of blood and albumin, as the irrigation fluid, view of recent findings that saline solutions tend to cause a decrease in the fibrinolytic activity of the venous endothelium. Some practitioners nevertheless prefer a clear irrigation fluid, and where such a fluid is desired, a colloidal solution having an oncotic pressure and pH similar to human blood should be chosen. One acceptable example is a 5% solution of albumin in a balanced electrolyte solution with normal pH.

With the valving assembly 30 and the pressure limiting device 40 attached to the syringe 20 as shown, a portion of the irrigation fluid in the syringe is injected into the valving assembly 30 and the pressure limiting device 40, with the nozzle 22 of the syringe held upwardly at about a 45° angle, the resilient reservoir 54 oriented downwardly, and with the stopcock 36, of course, open. This portion of the fluid (approximately 15 cc when a reservoir of the dimensions given below is used) should be sufficient to fill completely the valving member 30 and the pressure-limiting device 40, including the reservoir 54.

Thus primed, the syringe/valving member/pressure-limiting device assembly is attached to the cannula 70 which has been inserted into the upstream end of the harvested vein segment, as previously described. The vein segment is now irrigated to flush out any occlusions or blood clots, by injecting a small amount of irrigating fluid into the vein. After flushing is completed, the open downstream end of the vein segment is closed, for example with an atraumatic surgical clamp 120 (FIG. 4) and the vein, completely or at least partially filled with fluid, is now prepared for distention.

As the vein segment is filled with irrigation fluid, the pressure within the vein rises. If the force or pressure applied to the syringe plunger is carefully controlled, the pressure within the vein will not exceed that which is necessary to overcome spasm and to detect leaky side branches (designated by the numeral 130 in FIG. 4) which are then tied off or secured by ligature 140.

However, as previously mentioned, it is normally very difficult for the operator to know when a safe hydrostatic pressure level in the vein segment has been exceeded via the application of excessive force to the syringe plunger. With the present invention, however, this problem is avoided through the use of the expandable reservoir 54 of the pressure-limiting device 40. This results from the fact that the balloon-like reservoir is specifically designed to expand or inflate when the pressure in the vein (transmitted to the reservoir 54 via the cannula 70) exceeds a predetermined maximum value. Thus, in one mode of operation of the invention, the expansion of the resilient reservoir 54 serves as a warning indicator to the operator that the predetermined maximum pressure had been reached and that no more force should be applied to the plunger 21.

Even if the warning presented by the inflated reservoir 54 is ignored, and further pressure is applied to the plunger, the reservoir will continue to inflate without increasing the pressure in the vein segment. Thus, the pressure applied to the vein segment is limited to the maximum pressure required to inflate the reservoir. This maximum pressure is, of course, dependent solely upon the physical characteristics of the reservoir.

As previously noted, it has been shown that a distention pressure of between 100 and 400 mm Hg is usually necessary for effective elimination of vein spasm and revelation of leaky side branches. Thus, the characteristics of the reservoir can be selected so that the reservoir has a predetermined peak inflation pressure of somewhere between 100 and 400 mm Hg.

Figure 5:
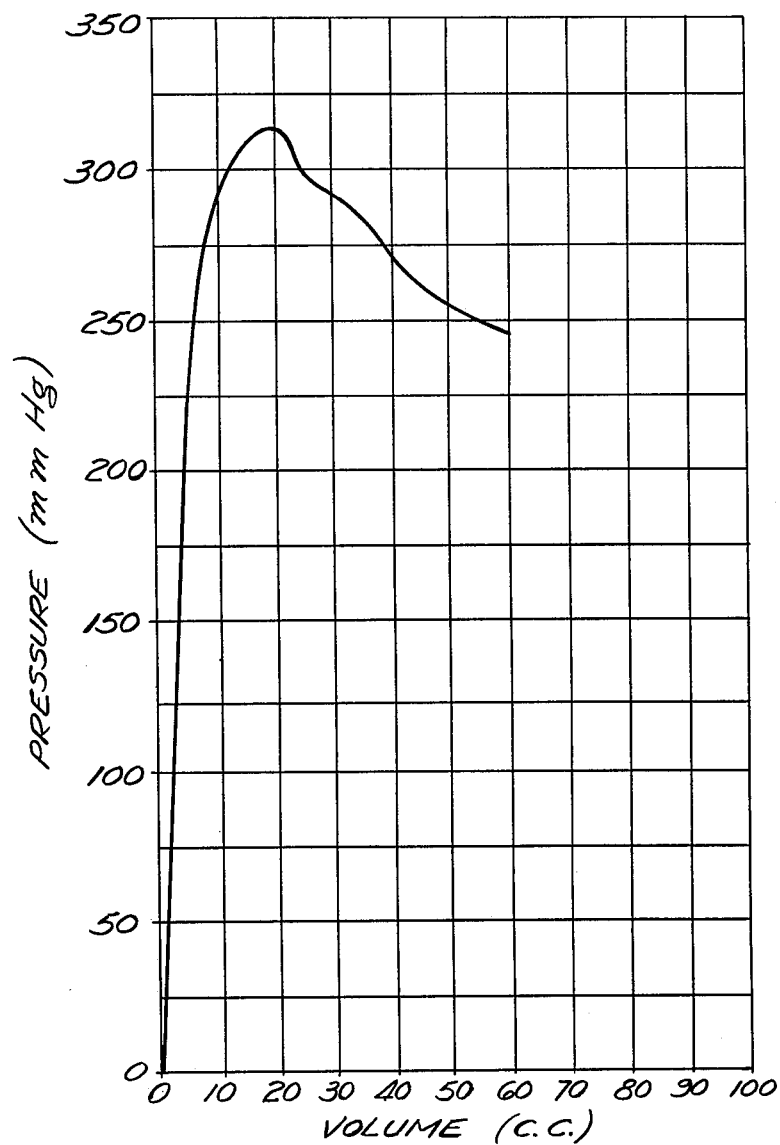
FIG. 5 is a graphical representation of typical pressure versus volume characteristics of the pressure-limiting device used in the present invention.

By way of specific example, pressure versus volume curves for several representative prototypes of the pressure-limiting device were generated during experimental testing procedures, and the curve illustrated in FIG. 5 represents the average of these curves. It can be seen that for these particular prototypes a peak pressure of approximately 315 mm Hg was generated, on the average, and this pressure was reached when the reservoir was filled with approximately 20 cc of fluid. Further filling of the reservoir resulted in a decrease in pressure, so that when the reservoir was filled to the capacity of the syringe (i.e., about 60 cc) a pressure slightly less than 250 mm Hg was generated.

The reservoir used in these tests was approximately spherical, as shown in the drawings, with a maximum outside diameter of approximately 3.2 cm and a wall thickness of approximately 33 mils (0.84 mm). The composition of the reservoir was natural rubber latex, of the type marketed by B. F. Goodrich Company under the designation "Compound 60LA298B". The cured film physical properties of this compound are as follows:

Tensile strength: 4000–5000 psi
Tear strength: 300–350 psi
Elongation (Elasticity): 750–900%

Should a peak pressure of approximately 400 mm Hg be desired, the wall thickness of the reservoir can simply be increased, the peak inflation pressure being roughly proportional to the wall thickness. Thus, it has been determined that a reservoir having dimensions and composition identical to those described above, except having a wall thickness of about 44 mils (1.1 mm) will exhibit a peak pressure of approximately 400 mm Hg, when the state of cure of the rubber is appropriately chosen and controlled.

It will be understood that reservoirs providing other peak pressures in the range of 100 to 400 mm Hg can be constructed utilizing differing wall thicknesses and compositions and states of cure. Thus, it will be appreciated by those skilled in the art that a reservoir having the requisite pressure versus volume characteristics can be constructed from a variety of resilient, rubber-like materials, with the dimensions of the reservoir being dictated by the physical characteristics of the material and by the particular peak pressure desired.

The stopcock 36 in the valving assembly 30 allows the use of another mode of operation of the invention. In this procedure, after the vein has been irrigated and filled with irrigation fluid, the reservoir 54 is gradually filled and inflated with the remaining contents of the syringe while the pressure-limiting device is attached to the cannula in the vein. When the reservoir is fully inflated, the stopcock 36 is closed. The reservoir is now self-pressurized at a predetermined pressure (depending on the volume of fluid therein), and it will continually deliver fluid to the vein (through the cannula) at approximately this predetermined pressure, which will never exceed the predetermined peak pressure. Moreover, the fluid is delivered automatically, without the need for the continued application of force on the plunger of the syringe. Thus, the operator has both hands free to tie off unsecured side branches.

As previously mentioned, complete dilation of the vein may require momentary pressures in excess of 400 mm Hg. Such transient pressures can be achieved by intermittently squeezing the reservoir, preferably with the stopcock closed. In addition, localized areas of persistent spasm can be distended, without subjecting the entire vein to excessive pressure, by digitally compressing the vein on both sides of the involved segment, and "milking" the entrapped fluid centispetally toward the center. This transiently raises the pressure in the affected segment only as high as necessary to overcome spasm, and the pressure is released as soon as the vein dilates. Again, this procedure is preferbly performed with the stopcock closed, so that the operator has both hands free to perform the "milking" while fluid is continuously delivered to the vein under controlled pressure.

From the foregoing description of the invention and its manner of use, it will be appreciated that the invention offers the following advantages:

1. Reliable limitation of venous hydrostatic pressure within a safe, but effective, pressure range.

2. Capability for automatic distention, allowing the operator to have both hands free for securing side branches and for dilating local areas of acute spasm.

3. Safe, quick, essentially non-traumatic cannulation, with good cannula retention within the vein.

4. Capability for delivering brief, high pressure transients to the vein for complete dilation without trauma.

The net results of these advantages are (a) a dramatic increase in the speed and safety with which the vein can be prepared for grafting; and (b) a substantially diminished risk of premature loss of patency in the grafted vein, with a resultant increase in the success rate of the arterial bypass or other procedure using the venous graft.

What is claimed is:

1. Apparatus for distention of a vein segment under controlled pressure, comprising:
   a syringe for containing an irrigation fluid;
   a cannula for introducing said fluid from said syringe into said vein segment; and
   means exterior of said vein segment connecting said syringe and said cannula and providing a fluid path therebetween, for limiting the hydrostatic pressure of said fluid in said vein to a predetermined maximum as said fluid is introduced into said vein, said maximum pressure being independent of either the pressure applied to said syringe or the rate of flow of said fluid from said syringe into said cannula, said maximum pressure being determined substantially solely by the physical characteristics of said pressure limiting means.

2. The apparatus of claim 1, wherein said pressure-limiting means comprises:
   an inlet connected to said syringe;
   an outlet connected to said cannula; and
   a resilient, expandable reservoir connected between said inlet and said outlet, the physical characteristics of said reservoir determining said maximum pressure.

3. The apparatus of claim 1, wherein said pressure-limiting means comprises:
   automatic fluid delivery means for first receiving fluid from said syringe and then delivering said fluid to said cannula at a predetermined pressure without the application of pressure to said syringe.

4. The apparatus of claim 3, wherein said automatic fluid delivery means comprises:
   reservoir means for receiving said fluid from said syringe and containing said fluid at a predetermined pressure; and valving means for selectively blocking fluid flow between said syringe and said reservoir means so that fluid is delivered to said cannula from said reservoir means at said predetermined pressure.

5. The apparatus of claim 2, wherein said pressure-limiting means further comprises:
valving means connected between said reservoir and said syringe, for selectively (a) permitting said reservoir to be expanded to a predetermined pressure with fluid from said syringe, and (b) permitting said fluid to be delivered to said cannula from said reservoir at said predetermined pressure.

6. Apparatus for distention of a harvested vein segment under controlled pressure, comprising:
a source of irrigation fluid;
means for delivering said fluid from said source into said vein segment at a pressure which is sufficient to overcome substantially all spasm in said vein segment, and which causes the least possible damage to the tissues in the vein segment consistent with the need to overcome spasm and identify leaks, said delivering means limiting said pressure to a predetermined maximum.

7. The apparatus of claim 6, where said source of irrigation fluid includes a syringe having a plunger for dispensing fluid in response to the application of pressure, and said fluid-delivering means includes means for selectively (a) limiting the hydrostatic pressure transmitted to said vein segment by said plunger to a predetermined maximum, and (b) receiving said fluid from said syringe and automatically delivering said fluid to said vein segment at a substantially constant, controlled pressure without the application of pressure to said plunger.

8. The apparatus of claim 4, wherein said fluid-delivering means includes manually-actuated means for generating transient pressures in said vein segment in excess of said predetermined maximum.

9. The apparatus of claim 8, wherein said manually-actuated means comprises:
a stopcock connected to, and in fluid communication with, said syringe; and
a resilient, expandable reservoir connected to, and in fluid communication with, said stopcock and said vein segment, such that when said stopcock is open, said reservoir is filled with fluid from said syringe and when said stopcock is then closed, said reservoir delivers said fluid to said vein segment automatically at a substantially constant controlled pressure, and the manual squeezing of said reservoir produces said transient pressures.

10. The apparatus of claim 9, wherein said reservoir is adapted to expand at a predetermined pressure when filled with fluid from said syringe, said expansion thereby limiting the hydrostatic pressure generated in said vein segment in response to the pressure applied to said plunger.

11. Apparatus for distention of a harvested vein segment with fluid from a syringe, comprising:
valving means connected to, and in fluid communication with, said syringe;
a resilient, expandable reservoir connected to, and in fluid communication with, said valving means; and
conduit means for delivering said fluid from said reservoir into said vein segment.

12. A method for preparing a harvested vein segment for grafting, comprising the steps of:
(1) inserting a cannula into the upstream end of said vein segment;
(2) attaching a syringe filled with irrigation fluid to the inlet of a resilient reservoir through a stopcock;
(3) filling said reservoir through said stopcock with fluid from said syringe;
(4) attaching the outlet of said reservoir to said cannula;
(5) flushing and filling said vein segment through said cannula with additional fluid from said syringe;
(6) closing the downstream end of said vein segment;
(7) when said vein segment is filled with fluid, inflating said resilient reservoir with the remaining fluid in said syringe so that said reservoir is pressurized with a predetermined pressure;
(8) closing said stopcock; and
(9) allowing said reservoir automatically to deliver said fluid to said vein segment through said cannula at said predetermined pressure to overcome spasm and to reveal unsecured side branches in said vein segment.

13. A method for preparing a harvested vein segment for grafting, comprising the steps of:
(1) inserting a cannula into the upstream end of said vein segment;
(2) flushing said vein segment with irrigation fluid through said cannula to remove residual air and particulate matter;
(3) closing the downstream end of said vein segment; and
(4) distending said vein segment with irrigation fluid at a pressure sufficient to overcome substantially all vein spasm and to reveal substantially all unsecured side branches without unnecessary trauma to the vein wall tissue.

14. The method of claim 13, wherein said distending of said vein segment with irrigation fluid is performed at a pressure in said vein segment not substantially less than 100 mm Hg and not substantially more than 400 mm Hg.

15. The method of claim 14, further comprising the step of:
(5) intermittently and controllably causing the pressure in said vein segment substantially to exceed 400 mm Hg for short time durations to relieve acute spasm in said vein segment.

16. The method of claim 13, wherein said distending step is performed by delivering said irrigation fluid to said cannula automatically and at a substantially constant controlled pressure from a resilient reservoir prepressurized by inflation with said fluid.

17. The method of claim 16, further comprising the step of:
(5) intermittently squeezing said reservoir manually to produce short-duration transient pressures substantially higher than said controlled pressure.

18. The apparatus of claim 1, wherein said physical characteristics of said pressure limiting means are such that said predetermined pressure is approximately 300 millimeters of mercury.

* * * * *

UNITED STATES PATENT AND TRADEMARK OFFICE
CERTIFICATE OF CORRECTION

PATENT NO. : 4,329,985
DATED : May 18, 1982
INVENTOR(S) : Lawrence I. Bonchek

It is certified that error appears in the above-identified patent and that said Letters Patent are hereby corrected as shown below:

Claim 18 should be deleted on Line 61 through 64 of Column 10.

Signed and Sealed this

Fifth Day of March 1985

[SEAL]

Attest:

DONALD J. QUIGG

Attesting Officer     Acting Commissioner of Patents and Trademarks